United States Patent
Pering et al.

(10) Patent No.: US 6,707,958 B2
(45) Date of Patent: Mar. 16, 2004

(54) BIOCHEMICAL ASSAY DEVICE USING FRUSTRATED TOTAL INTERNAL REFLECTION MODULATOR WITH AN IMAGING OPTICAL WAVEGUIDE

(75) Inventors: Richard D. Pering, Mountain View, CA (US); David A. King, Menlo Park, CA (US); Richard J. Pittaro, San Carlos, CA (US); Shahida Rana, Fremont, CA (US); Frederick A. Stawitcke, Sunnyvale, CA (US); Edward D. Verdonk, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 278 days.

(21) Appl. No.: 09/988,468

(22) Filed: Nov. 20, 2001

(65) Prior Publication Data

US 2003/0095764 A1 May 22, 2003

(51) Int. Cl.⁷ ............................ G02B 6/00; G01N 21/29
(52) U.S. Cl. ................... 385/12; 385/18; 422/85.05; 435/288.7
(58) Field of Search .................. 385/12, 13, 16–18, 385/39, 40, 147; 422/82.05, 82.06, 82.07, 82.08, 82.09, 82.11; 435/288.7, 808

(56) References Cited

U.S. PATENT DOCUMENTS

| | | | |
|---|---|---|---|
| 3,980,395 A | * 9/1976 | Giallorenzi et al. | 349/196 |
| 4,857,273 A | * 8/1989 | Stewart | 422/82.11 |
| 5,082,629 A | * 1/1992 | Burgess et al. | 422/82.11 |
| 5,165,005 A | * 11/1992 | Klainer et al. | 385/129 |
| 5,349,443 A |   9/1994 | Guerra | |
| 5,369,718 A |   11/1994 | Kamata et al. | |
| 5,452,385 A | * 9/1995 | Izumi et al. | 385/37 |
| 6,110,749 A | * 8/2000 | Obremski et al. | 436/527 |
| 6,122,394 A |   9/2000 | Neukermans et al. | |
| 6,181,367 B1 |   1/2001 | McGrew et al. | |
| 6,236,778 B1 | * 5/2001 | Laughlin | 385/24 |
| 6,249,370 B1 | * 6/2001 | Takeuchi et al. | 359/291 |
| 6,432,364 B1 | * 8/2002 | Negami et al. | 422/82.11 |
| 6,483,096 B1 | * 11/2002 | Kunz et al. | 250/214 R |
| 6,534,011 B1 | * 3/2003 | Karthe et al. | 422/82.01 |

FOREIGN PATENT DOCUMENTS

WO     WO 9503538 A1 * 2/1995     G01N/21/77

* cited by examiner

*Primary Examiner*—Akm Enayet Ullah
*Assistant Examiner*—Michelle R. Connelly

(57) ABSTRACT

A biochemical assay device optically scans individual biological sample containing wells in an assay plate. The device includes an imaging system overlaying the assay plate wherein a scanning light propagates by total internal reflection within an optical waveguide. The waveguide includes a plurality of pixel locations, each aligned with a well in the assay plate, at which total internal reflection is selectively frustrated to output an incident beam of light. That light illuminates the well and causes generation of an emission beam of light that is detected by a photoreceptor. The device further includes a driver circuit that controls the selective frustration of total internal reflection at each pixel location in order to scan each well in the assay plate. A processor is also included in the device to process the detected emission beams of light generated by the scanned wells for purposes of assaying the biological sample contained in each scanned well.

28 Claims, 3 Drawing Sheets

BIOCHEMICAL ASSAY DEVICE USING FRUSTRATED TOTAL INTERNAL REFLECTION MODULATOR WITH AN IMAGING OPTICAL WAVEGUIDE

BACKGROUND OF THE INVENTION

1. Technical Field of the Invention

The present invention relates to a device for conducting a biochemical assay and, in particular, to such a device configured for optical scanning of biochemical sensor wells in a testing assay plate.

2. Description of Related Art

Biomedical assaying techniques are well known in the art. Fluorescence comprises one well known transduction method. In this technique, a biological material sample (such as blood, feces, urine, and the like) under examination undergoes a biochemical reaction at a biochemical sensor well. This chemical reaction generally involves applying one or more reagents to the deposited biological material sample. The reagent(s) is (are) selectively chosen based on a known reaction with a component (for example, a protein) of interest that may or may not be present in the biological material sample to produce a chemical analyte having fluorescing properties. Furthermore, the amount of analyte produced by the chemical reaction is typically proportional to the amount of the component of interest that is present in the deposited sample. The biochemical sensor well is then exposed to light having a known and controlled wavelength and intensity for exciting the analyte, and the resulting fluorescent light emitted by the excited analyte is measured to obtain information indicative of the amount of analyte produced by the chemical reaction. From this information a deduction may be made concerning the amount of the included component of interest contained within the sample.

Complex biochemical assays are preferably performed in an array format wherein a plurality of biochemical sensor wells (also referred to as "test cells") are arranged on an assay plate in an n×m format to allow for the simultaneous testing of plural samples and control groups. An assay reading device is then used to optically scan each of the individual biochemical sensor wells. This scanning operation generally involves the use of a robotic device that moves an ultraviolet illumination device and fluorescent reading device about the plate array from well to well to individually measure emitted fluorescence. From these measurements, a determination may be made of the amount of chemical analyte that is present. This information is then used to obtain an indication of the presence of and the amount of the component of interest that is contained in the sample.

The robotic assay scanning devices known in the art typically include a number of moving parts relating to the illumination device and to the reading device. These moving components are highly susceptible to wear and breakdown. The robotic nature of these devices further significantly adds to the cost of device production and maintenance. These devices can also be quite large in size, and are not easily modified into the compact, smaller form factors that are required for portability. Still further, these robotic devices often inefficiently utilize physically separate illumination and detection components.

What is needed is a biochemical assay device utilizing no moving parts that is suitable for implementation in a very compact form factor. There would also be an advantage if the device utilized a common, perhaps integrated, optical source/detector.

SUMMARY OF THE INVENTION

The present invention concerns an imaging system that utilizes an optical waveguide for scanning. A scanning light beam propagates through the optical waveguide by total internal reflection. A refractive index modulator is positioned adjacent waveguide and includes a plurality of optical doors. Each optical door is selectively configurable into either a first refractive condition or a second refractive condition. In the first refractive condition, the optical door has a first index of refraction that continues total internal reflection of the scanning beam. In the second refractive condition, the optical door has a second index of refraction which frustrates total internal reflection and allows the scanning light beam to exit the optical waveguide through the optical door. The exiting scanning light beam is used to illuminate a scanned object with an incident beam of light. The scanned object responds to illumination by generating an emission beam of light that is detected by a photoreceptor.

Embodiments of the present invention still further comprise a biochemical assay device that optically scans individual biological sample containing wells in an assay plate. The device includes an imaging system overlaying the assay plate wherein a scanning light propagates by total internal reflection within an optical waveguide. The waveguide includes a plurality of pixel locations, each aligned with a well in the assay plate, at which total internal reflection is selectively frustrated to output an incident beam of light. The incident beam of light illuminates the well causing generation of an emission beam of light that is received at the pixel location and propagated in the waveguide. A photoreceptor detects the emission beam of light from each illuminated well. The device further includes a driver circuit that controls the selective frustration of total internal reflection at each pixel location in order to scan each well in the assay plate with an incident beam of light. A processor is also included in the device to process the detected emission beams of light generated by the scanned wells for purposes of assaying the biological sample contained in each scanned well.

Embodiments of the present invention still further comprise a method for optically scanning individual wells in an assay plate. A light propagating substrate is positioned overlaying the assay plate. The substrate includes a plurality of pixel locations, with each pixel location being aligned with a well in the assay plate. A scanning light then propagates within the light propagating substrate by total internal reflection. The total internal reflection of the scanning light is then selectively frustrated at each pixel location to output from the light propagating substrate an incident beam of light at each pixel location that illuminates each of the wells in the assay plate. Responsive to the incident beam of light, each illuminated well generates an emission beam of light that is detected.

BRIEF DESCRIPTION OF THE DRAWINGS

A more complete understanding of the method and apparatus of the present invention may be acquired by reference to the following Detailed Description when taken in conjunction with the accompanying Drawings wherein.

DETAILED DESCRIPTION OF THE PRESENT INVENTION

Figure 1:
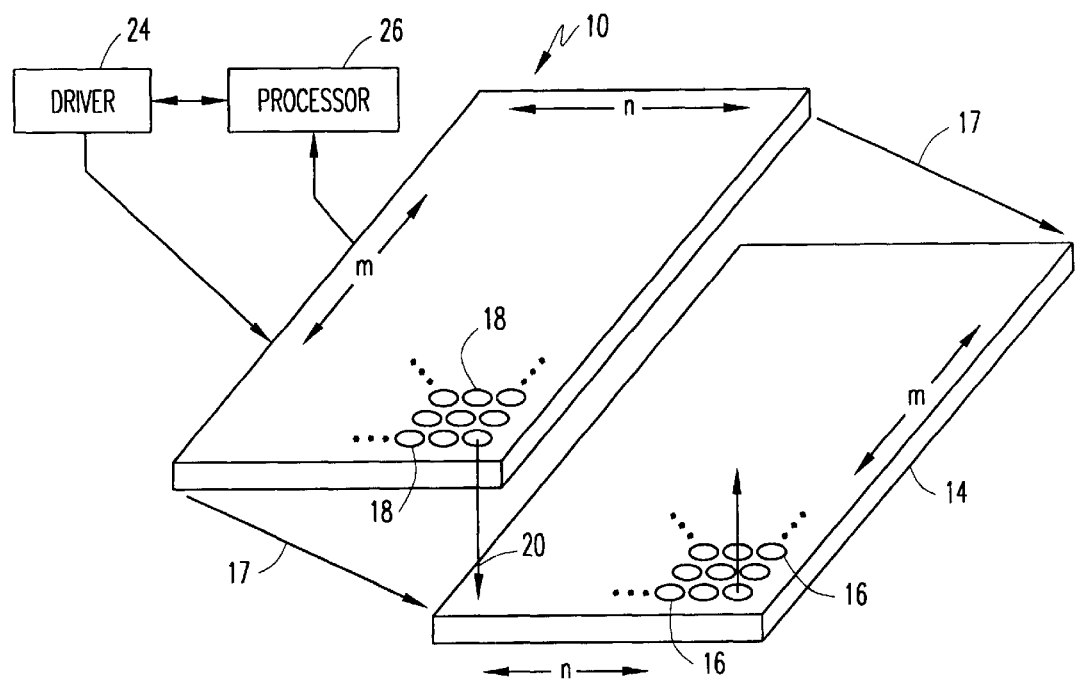
FIG. 1 is a block diagram of a biochemical assay device in accordance with an embodiment of the present invention.

Reference is now made to FIG. 1 wherein there is shown a block diagram of a biochemical assay device in accordance with an embodiment of the present invention. The device 10 includes an imaging system 12 used to optically scan a biochemical testing assay plate 14. This testing plate 14 includes a plurality of individual biochemical sensor wells 16 arranged an n×m array format. At each of these sensor wells 16, a biochemical reaction may occur that results in the production of an analyte in quantities generally proportionate to the amount of a certain component (for example, a protein) of interest that may or may not be included within a biological material sample deposited in the well. The imaging system 12 is operable to scan over the assay plate 14 and optically detect the presence of the analyte at each one of the included biochemical sensor wells 16. To accomplish this goal, the imaging system 12 includes an array of imaging pixel locations 18 (shown for clarity in FIG. 1 on a reverse side of the imaging system 12) that are arranged in an n×m format that matches and aligns with the well 16 locations on the assay plate 14. This allows the imaging system 12 to overlay the assay plate 14 as generally shown by the arrows 17 in FIG. 1 during the scanning operation. Advantageously, this overlay 17 keeps foreign particles from entering and possibly contaminating the wells 16, and further helps minimize concerns over reading errors caused by the adverse effects of ambient light. Photons of light having a certain wavelength are then selectively output as an incident beam of light 20 from each pixel location 18. Raster or other appropriate scanning techniques may be used to sequentially illuminate each correspondingly positioned biochemical sensor well 16 in the biochemical assay plate 14. Responsive to this illumination by the incident beams of light 20, photons of light (having the same or a different wavelength) are generated from each scanned biochemical sensor well 16 as an emission beam of light 22. As one example, the analyte may have fluorencent characteristics in which case the emission beam of light 22 comprises fluorescent photons emitted from the analyte responsive to excitation by the incident beam of light 20. In another example, the analyte may cause a color, shade or hue change or shift on a well test surface in which case the emission beam of light 22 comprises a reflection of the incident beam of light 20 as modified in accordance with that change or shift. Each emission beam of light 22 is received by the imaging system 12 at the same pixel location 18 where its inducing emission beam of light 20 was output. As an alternative illustrated in FIG. 8, the incident beam of light 20 and the emission beam of light 22' may be handled by different (normally adjacent) pixel locations 18. The emission beam of light 22 is then detected by the imaging system 12 to generate a data signal (in either an analog or digital format) having a magnitude that is proportionate to measured light intensity.

The device 10 further includes a driver circuit 24 operable to control the operation of the imaging system to produce the incident beams of light 20 (perhaps, sequentially) and optically scan each well 16 in the biochemical testing assay plate 14. Scanning drivers of this sort for controlling the operation of the imaging system 12 are well known in the art. Furthermore, a brief description of two possible embodiments for the driver circuit is provided herein in connection with the discussion of FIGS. 4 and 7. The device 10 still further includes a data processing circuit 26 synchronized for operation with the driver circuit 24 and operable to store and process the data signals output from the imaging system 12 concerning the received emission beams of light 22 that are detected for each pixel location 18. Data processors of this sort are also well known in the art. For example, the processor used by prior art robotic-type readers may be advantageously reused in connection with the device 10. Configuration and construction of such a processing unit for assaying is well within the ability of one skilled in art and thus a detailed description herein is not deemed necessary.

Figure 2:
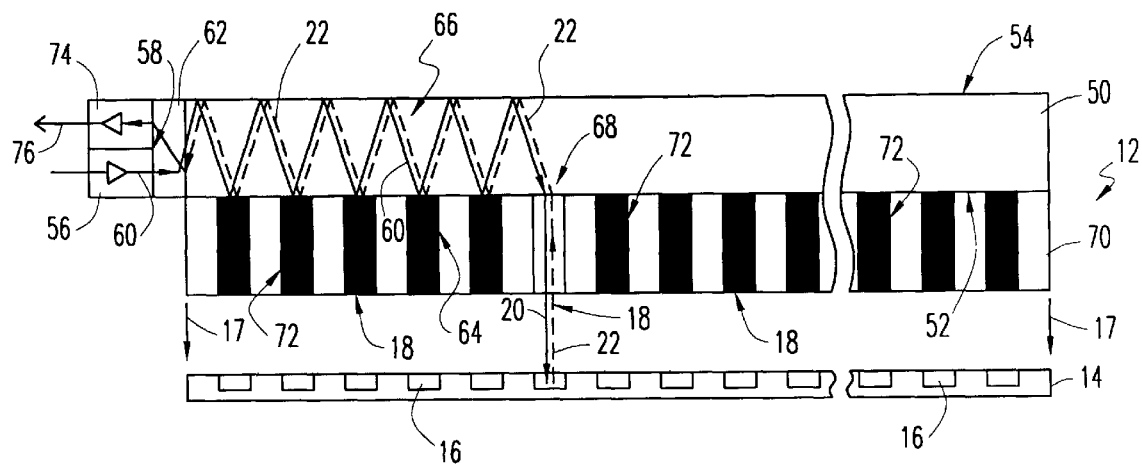
FIG. 2 is a block diagram for an embodiment of an imaging system within the biochemical assay device shown in FIG. 1.

Reference is now made to FIG. 2 wherein there is shown a block diagram for an embodiment of the imaging system 12 for the biochemical assay device 10 of FIG. 1. The imaging system 12 includes an optical waveguide 50 (not necessarily drawn to scale) of a high refractive index transparent material (for example, at or about 1.68). The waveguide 50 is preferably planar (and as thin as possible), but may have other shapes as desired to match the shape/contour of the biochemical testing assay plate 14. The waveguide 50 has a front surface 52 and a rear surface 54 The front surface 52 faces in the direction of the biochemical testing assay plate 14 to be scanned. A light generator 56 is mounted along an edge 58 of the waveguide 50 to generate a scanning light 60. The light generator 56 may comprise a single point source or a plurality of point sources as desired and required for the given size of the waveguide 50 and corresponding size of the to be scanned assay plate 14. Generally speaking, the light generator 56 comprises one or more laser diodes or light emitting diodes (LEDs) as point sources for generating the scanning light 60 having a certain desired wavelength for a given transduction method. In the event plural light sources are used, they are preferably spaced apart from each other in a linear array, and furthermore may be configured in number and arranged in a manner substantially corresponding to the spacing along the same dimension between the n or m plurality of included wells 16.

The scanning light 60 generated by the light generator 56 is coupled to the waveguide 50 through an optical coupler 62. The coupler 62 is configured, positioned and oriented in a manner such that the scanning light 60 is diffracted at a sufficient angle (for example, at or about 72 degrees where the waveguide is made from a high refractive index transparent material, such as flint glass or glass containing a high lead content) to cause the scanning light to propagate through the waveguide 50 with total internal reflection (TIR) from the interfaces formed at the front and rear surfaces 52 and 54, respectively, of the waveguide. Any suitable optical coupler 62 may be utilized including one or more of the following exemplary selections: orienting the light generator at the proper angle; a holographically formed diffractive element; a prism; a lens; and the like.

Although illustrated positioned on the edge 58 of the waveguide 50, it will be understood that the light generator 56 (along with optical coupler 62) may alternatively be positioned along the front or rear surfaces, 52 or 54, respectively, of the waveguide so long as the scanning light 60 is directed into the waveguide at the proper angle to produce a known pattern of periodic bounces of the light 60 (see, generally, at reference 66) due to total internal reflection. Within a certain range, the bounce rate for the scanning light 60 due to total internal reflection may be adjusted to align at least some of the reflection points at the surface 52 of the waveguide substantially with the location of wells 16 within the assay plate 14 thus assisting with the definition of pixel locations 18.

The imaging system 12 further includes a refractive index modulator 70 positioned adjacent the front surface 52 of the waveguide 50 and serving to overlay 17 the assay plate 14. The modulator 70 (again, not necessarily drawn to scale) includes an n×m arrayed plurality of selectively actuatable optical doors 72 that coincide with the plurality of pixel locations 18. These optical doors 72 are substantially aligned with at least some of the total internal reflection points for the scanning light 60. The doors 72 within the modulator 70 are formed from a material having a refractive index that can be selectively controlled and electrically switched between high and low states. Examples of such materials include, but are not limited to, ferroelectric liquid crystal, nematic liquid crystal, electro-optic media, multiple quantum well media, electron trapping materials, photorefractive materials, and the like. When the material exhibits a relatively low index of refraction, the scanning light 60 propagating though the waveguide 50 is reflected (see, generally, at reference 64) at the location of the optical door 72 by the front surface 52 (i.e., the optical door is closed). However, when the material exhibits a relatively low index of refraction, total internal reflection of the scanning light 60 propagating though the waveguide 50 is frustrated at the location of the optical door 72 (i.e., the optical door is opened). Frustrated total internal reflection at this pixel location 18 allows the scanning light 60 to pass out of the waveguide (see, generally, at reference 68) and through the open door of the modulator 70 for purposes of generating the incident beam of light 20. Although a door 72 is illustrated at each reflection point for the scanning light 60 on the surface 52 of the waveguide 50, it will be understood that the doors need not be so configured and are preferably positioned to align not only with certain ones of the reflection points but also with the locations of wells 16 when the imaging system overlays 17 the assay plate 14 (see, for example, the configuration of FIG. 5).

When a properly aligned overlay 17 is established, the incident beam of light 20 output from a pixel location 18 illuminates a correspondingly positioned biochemical sensor well 16. Responsive to that illumination, photons of light having the same or a different wavelength and comprising the emission beam of light 22 are generated from the illuminated biochemical sensor well 16. It will, of course, be understood that light is emitted in many directions (and perhaps, omnidirectionally), with the emission beam of light 22 being only representative and exemplary of such emissions. As discussed above, this emission beam of light may comprise excited fluorescence or color reflection (or the like) due to the production and presence of a certain analyte within the well 16. The emission beam of light 22 is received at the corresponding pixel location 18 and passes through the open 68 optical door 72 back into the waveguide 50. Once in the waveguide 50, and assuming proper angular relationships are met, the emission beam of light 22 propagates, similarly taking advantage of the total internal reflection (TIR) characteristics of the waveguide 50, toward the optical coupler 62 in a reverse direction generally along the same path as that traveled by the scanning light 60. It is recognized that some propagation differences are likely, and the propagation illustrated for the paths of light 60 and beam 22 is exemplary only in nature. At the optical coupler 62, the emission beam of light 22 is coupled to a photoreceptor 74 where an output data signal (analog or digital) 76 is generated having a magnitude that is proportional to the measured intensity of the detected emission beam of light. It is likely that there will be some slight offsets and angular shifts (schematically illustrated in exaggerated fashion within the waveguide 50 by the offset solid and dotted light rays) between the scanning light 60 (solid ray) and the emission beam of light 22 (dotted ray). These offsets and shifts, however, are of little concern and may actually beneficially assist with the configuration and operation of the optical coupler 62 to separate the two light components and direct the received emission beam of light 22 accurately towards the photoreceptor 74. The photoreceptor 74 may comprise a single point photodiode or a plurality of photodiodes as desired (and typically matching the format of the point sources used in the light generator 56). Generally speaking, the photoreceptor 74 comprises one or more avalanche photodiodes having a configuration well known in the art. The photoreceptor 74 may further include an appropriate analog-to-digital conversion device (not explicitly shown) for the purpose of generating the output data signal 76 in a digital format.

Figure 3:
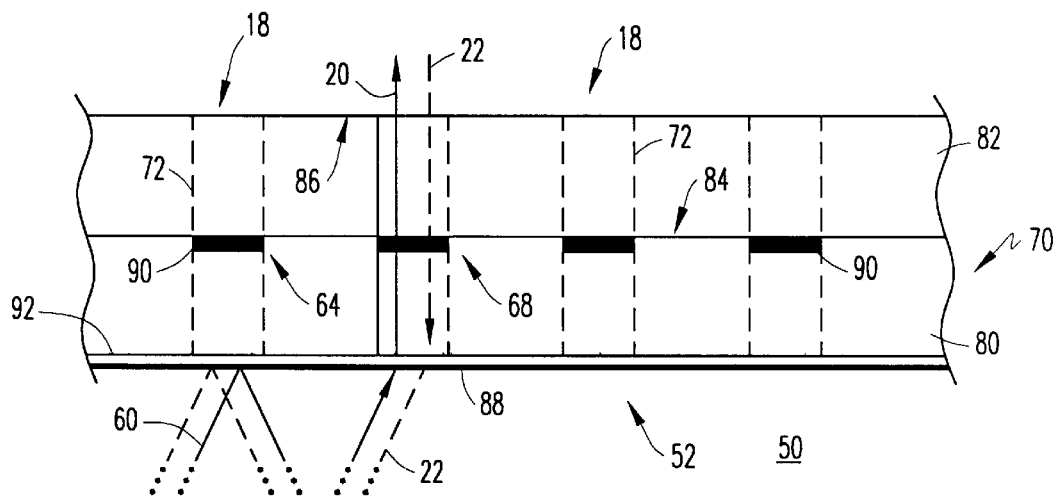
FIG. 3 is a cross-sectional diagram illustrating an embodiment of a total internal reflection, refractive index modulator suitable for use in the imaging system of FIG. 2.

Refractive index modulators 70, and more specifically, total internal reflection modulators, have many configurations that are well known to those skilled in the art. An example of one such modulator 70 is given in U.S. Pat. Nos. 5,973,727 and 6,181,367. The disclosures of these patent references are hereby incorporated by reference. As an example, a modulator 70 may have a cross-sectional configuration similar to that illustrated in FIG. 3 (and as described in more detail within the foregoing referenced patents). The modulator 70 covers the front surface 52 of the waveguide 50 with a layer of liquid crystal 80 positioned between the waveguide 50 and a cover plate 82. The cover plate includes a rear surface 84 and a front surface 86. A first electrode 88 is formed on the front surface 52 of the waveguide 50 while a plurality of second, strip, electrodes 90 are formed on the rear surface 84 of the cover plate 82. The strip electrodes 90 have a suitable width of and an inter-strip spacing that is substantially equal to the spacing between adjacent wells 16 in an assay plate 14. The electrodes 88 and 90 may be formed from a thin (for example, on the order of 1 micron or less) layer of indium tin oxide ("ITO") which is electrically conductive and transparent. A layer 92 of polymeric material is applied over the electrode 88 and its molecules are oriented in a predetermined direction to align the liquid crystal 80 layer to have an anisotropic refractive index that is optimized in a manner that maximizes the differences in refractive index measured with respect to the polarization of the scanning light 60 propagating in the waveguide 50. The cover plate 82 is preferably configured (through the use of a high index of refraction material relative to the index of refraction of the liquid crystal 80, or the use of a holographic optical coupling means) so that light passing through the liquid crystal easily propagates through the cover plate 82 rather than being reflected from the liquid crystal/cover plate interface at the surface 84.

When a voltage of a certain polarity is applied between a selected one of the strip electrodes 90 and the electrode 88, an electric field is generated and the molecules of the liquid crystal 80 adjacent the selected strip electrode 90 assume an alignment that is dependent upon the polarity of that electric field. In a first polarity associated with a first crystal alignment, the liquid crystal 80 exhibits a relatively low index of refraction (for example, 1.55) at the strip electrode location, and the scanning light 60 which is propagating by total internal reflection in the waveguide 50 is again reflected from the interface between the waveguide and the liquid crystal. In this condition, the optical door 72 is closed 64 causing continued scanning light 60 propagation along the waveguide 50. In a second polarity associated with a second crystal alignment, the liquid crystal 80 exhibits a relatively high index of refraction (for example, 1.64) at the strip electrode location, and the scanning light 60 propagating through the waveguide 50 is no longer reflected from the interface between the waveguide and the liquid crystal. In this condition, frustrated total internal reflection occurs at the strip electrode location, the optical door 72 is opened 68 and the scanning light 60 passes out of the waveguide 50 and through the liquid crystal 80 as the incident beam of light 20. Notably, this condition further allows for the emission beam of light 22 generated at the well 16 location in the assay plate 14 to pass back through the liquid crystal 80 and enter the waveguide 50. More specifically, it is recognized that a plurality of optical doors 72 along the length of the activated strip electrode 90 are opened. In this configuration, a selected point source is illuminated that is aligned with the specific pixel location of interest to be scanned. An alternative configuration for individually activating pixel locations 18 is discussed herein in connection with FIG. 6.

Figure 4:
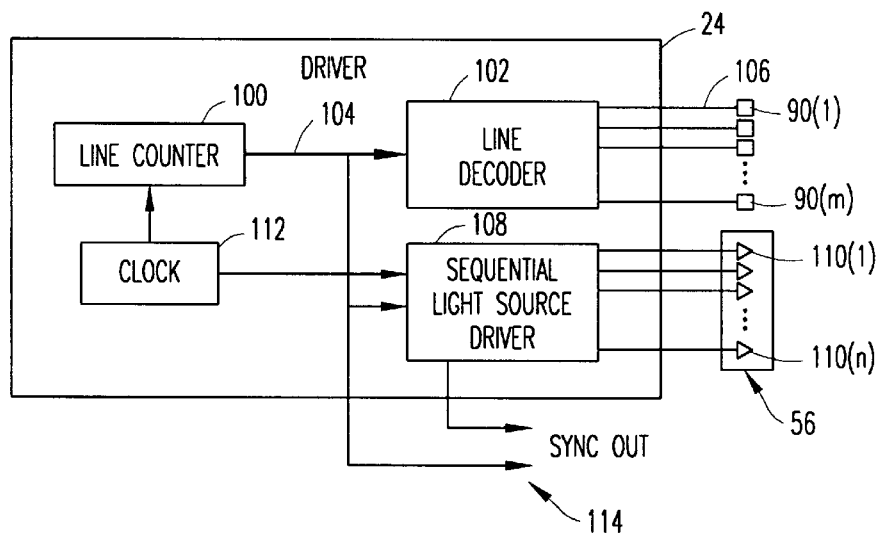
FIG. 4 is a simplified block diagram of one embodiment for a driver circuit for the imaging system of FIG. 2.

Reference is now made to FIG. 4 wherein there is shown a block diagram of the driver circuit 24. The driver circuit 24 operates to control the application of voltages to the electrodes 88 and 90. More specifically, a line counter 100 resets at the instigation of each scan, and then cycles from 1 to m to count through the number of electrodes 90. A line decoder 102 receives a digital signal 104 from the line counter 100 that corresponds to the count in the line counter. The digital signal 104 is then decoded to generate an electrode voltage signal 106 on one output at a time. Application of this electrode voltage signal 106, as discussed above, causes the second polarity (associated with a second alignment of the liquid crystal 80) to be applied between the selected strip electrode 90 and the electrode 88 which frustrates total internal reflection within the waveguide 50 and opens 68 each of the optical doors 72 located along that strip. Responsive to each line counter 100 digital signal 104, a light source driver 108 then sequentially (from 1 to n) energizes each point source 110 within the light generator 56 at a predetermined intensity to supply the scanning light 60. The pixel location 18 in the imaging system 12 array that corresponds to the intersection of the selected strip electrode 90 and path for the scanning light 60 emitted from the energized point source 110 then generates the incident beam of light 20 and allows for reception of the emission beam of light 22. The rate at which the line counter 100 increments to select electrodes 90 and the rate at which the driver 108 sequentially energizes the point sources 110(1)–110(n) (for each counted line) may be user selected, with control over such rate provided through a clock 112. Responsive to operation of the counter 100, decoder 102 and driver 108, the imaging system 12 effectively scans each well 16 on the assay plate 14. By repeating the foregoing process operation, multiple consecutive scans of the plate 14 may be performed. It will further be understood that the light source driver 108 may simultaneously energize each of the point sources 110 causing a plurality of incident beams of light 20 to be output from each pixel location 18 along the selected strip electrode 90. With this operation, a corresponding plurality of emission beams of light 22 will be simultaneously generated and propagated back through the waveguide 50, with the processor 26 (see, FIG. 1) operating to simultaneously capture or sequentially sample the corresponding plurality of data signals 76 output from the photoreceptors 74. The driver circuit 24 further outputs 114 one or more sync signals that provide information to the processor 26 concerning the strip electrode 90(1 to m) is currently being selected as well as providing information to the processor concerning which point source 110(1 to n) is currently being energized. This information is used by the processor to correlate received data signals 76 as output from the photoreceptors 74 of the imaging system 12 with the scanning operation being implemented by the driver circuit 24.

Figure 5:
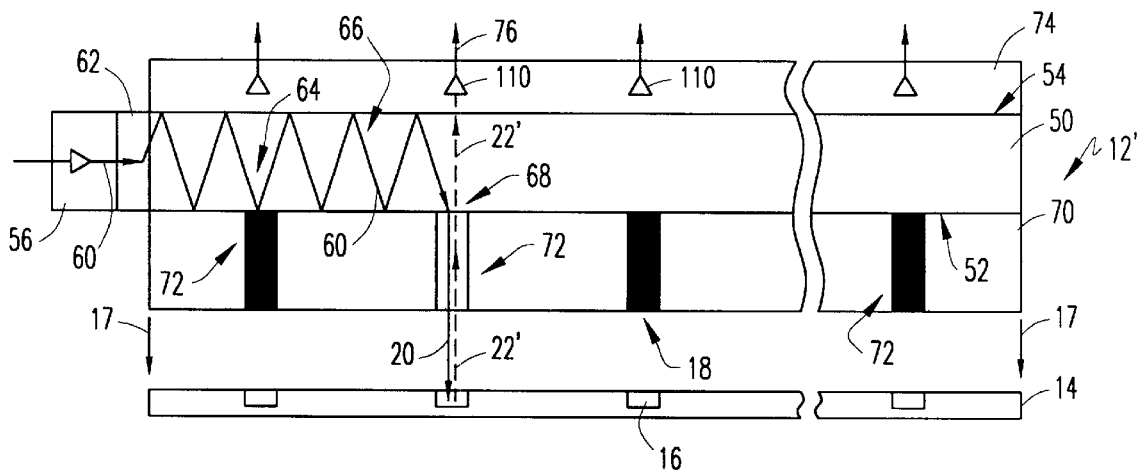
FIG. 5 is a block diagram for another embodiment of an imaging system within the biochemical assay device shown in FIG. 1.

Reference is now made to FIG. 5 wherein there is shown a block diagram for another embodiment of the imaging system 12' for the biochemical assay device 10 of FIG. 1 (where identical reference numbers refer to identical components). The imaging system 12' includes an optical waveguide 50 having front and rear surfaces, 52 and 54, respectively. A light generator 56 is mounted along an edge 58 of the waveguide 50 to generate a scanning light 60. The scanning light 60 generated by the light generator 56 is coupled to the waveguide 50 through an optical coupler 62 and propagated therein with total internal reflection (TIR) from the interfaces formed at the front and rear surfaces, 52 and 54, respectively, of the waveguide. The refractive index modulator 70 positioned adjacent the front surface 52 of the waveguide 50 includes an array of selectively actuatable optical doors 72 each defining a pixel location 18. When the door 72 is closed, the scanning light 60 propagating though the waveguide 50 is reflected (see, generally, at reference 64) by the front surface 52. However, when the door 72 is opened, total internal reflection of the scanning light 60 propagating though the waveguide 50 is frustrated at the pixel location 18 allowing the scanning light 60 to pass out of the waveguide (see, generally, at reference 68) as the incident beam of light 20. When a properly aligned overlay 17 with the wells 16 of the assay plate 14 is established, the incident beam of light 20 illuminates a correspondingly positioned biochemical sensor well 16, and photons of light comprising the emission beam of light 22' are generated. The emission beam of light 22' is received at the corresponding pixel location 18, passes through the waveguide 50, and exits through the rear surface 54. At the rear surface 54, the emission beam of light 22' is coupled to a photoreceptor 74 where an output data signal (analog or digital) 76 is generated having a magnitude that is proportional to the measured intensity of the detected emission beam of light. The photoreceptor 74 includes an array of photodiodes (or example, avalanche photodiodes) positioned substantially matching the position, and further in alignment with, the location of the optical doors 72. The photoreceptor 74 may further include an appropriate analog-to-digital conversion device (not explicitly shown) for the purpose of generating the output data signal 76 in a digital format. Alternatively, the photoreceptor 74' may be positioned on an opposite side of the plate 14 (as shown in dotted lines) to take advantage of emission beam of light 22' generation out the back side of the plate. An advantage of this embodiment is that it placed the photoreceptors 74, 74' closer to the wells 16.

Figure 8:
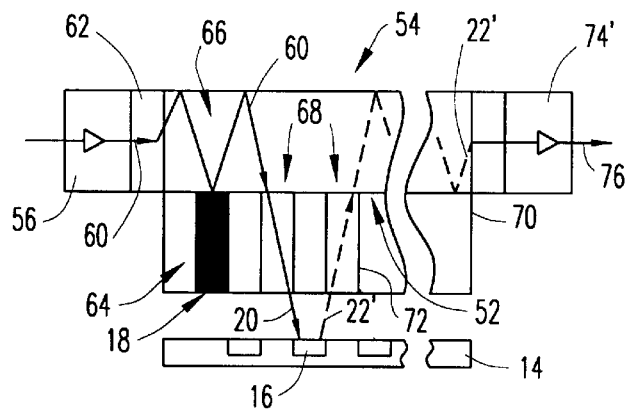
FIG. 8 is a block diagram for another embodiment of an imaging system within the biochemical assay device shown in FIG. 1.

As a further alternative, the emission beam of light 22' that is received at the corresponding pixel location 18 and passes through the open 68 optical door 72 back into the waveguide 50, and with proper angular relationships, is then propagated through the waveguide 50 by total internal reflection in the same direction as the scanning light 60. This is shown in FIG. 8. The photoreceptor 74' is then positioned on an opposite edge of the waveguide 50 from the light generator 56. It is also possible to propagate the received emission beam of light 22' by total internal reflection in a direction perpendicular to the propagation path for the scanning light 60. In this configuration, the photoreceptor 74' would be positioned on an adjacent edge of the waveguide 50 with respect to the location of the light generator 56. The illustration of FIG. 8 is to be construed to cover both of these propagation scenarios.

Figure 6:
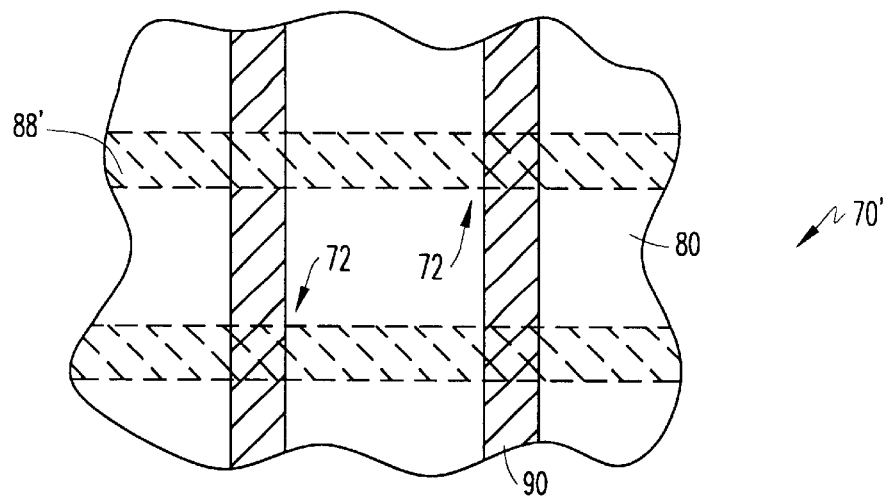
FIG. 6 is a partial top view of an embodiment of a total internal reflection, refractive index modulator suitable for use in the imaging system of FIGS. 2 and 5.

Reference is now made to FIG. 6 wherein there is shown a partial top view of a total internal reflection, refractive index modulator 70' suitable for use in the imaging system of FIGS. 2 and 5 (where identical reference numbers refer to identical components). FIG. 6 shows the layer of liquid crystal 80 which is positioned between the waveguide 50 and a cover plate 82 (see, FIG. 3). The cover plate includes a rear surface 84 and a front surface 86. A plurality of first strip electrodes 88' are formed on the front surface 52 of the waveguide 50 while a plurality of second strip electrodes 90 are formed on the rear surface 84 of the cover plate 82. The strip electrodes 88' and 90 are oriented perpendicularly to each other, with each strip electrode having a suitable width and an inter-strip spacing that is substantially equal to the spacing between adjacent wells 16 in an assay plate 14. The strip electrodes 88' and 90 may be formed from a thin (for example, on the order of 1 micron or less) layer of indium tin oxide ("ITO") which is electrically conductive and transparent. When a voltage of a certain polarity is applied between a selected one of the first strip electrodes 88' and a selected one of the second strip electrodes 90, an electric field is generated and the molecules of the liquid crystal 80 adjacent the intersection of those strips assume an alignment that is dependent upon the polarity of that electric field. With a first crystal alignment that exhibits a relatively low index of refraction at the strip electrode intersection location, the optical door 72 is closed at the intersection and the scanning light 60 which is propagating by total internal reflection in the waveguide 50 is again reflected from the interface between the waveguide and the liquid crystal. With a second crystal alignment, on the other hand, that exhibits a relatively high index of refraction at the strip electrode intersection location, the optical door 72 at the intersection is opened and the scanning light 60 propagating through the waveguide 50 is no longer reflected from the interface between the waveguide and the liquid crystal. In this condition, frustrated total internal reflection occurs at the strip electrode intersection location, and the scanning light 60 passes out of the waveguide 50 through the open door 72 as the incident beam of light 20. Notably, this condition further allows for the emission beam of light 22' generated at the well 16 location in the assay plate 14 to pass back through the liquid crystal 80 and enter the waveguide 50. Again, as discussed above and illustrated in FIG. 8, the emission beam of light 22' may alternative return back to the waveguide 50 through the open optical door 72 of a different, perhaps adjacent, pixel location 18. Furthermore, the emission beam of light 22' may propagate within the waveguide by total internal reflection (as shown in FIGS. 2 and 8) or pass through the waveguide (as shown in FIG. 5).

Figure 7:
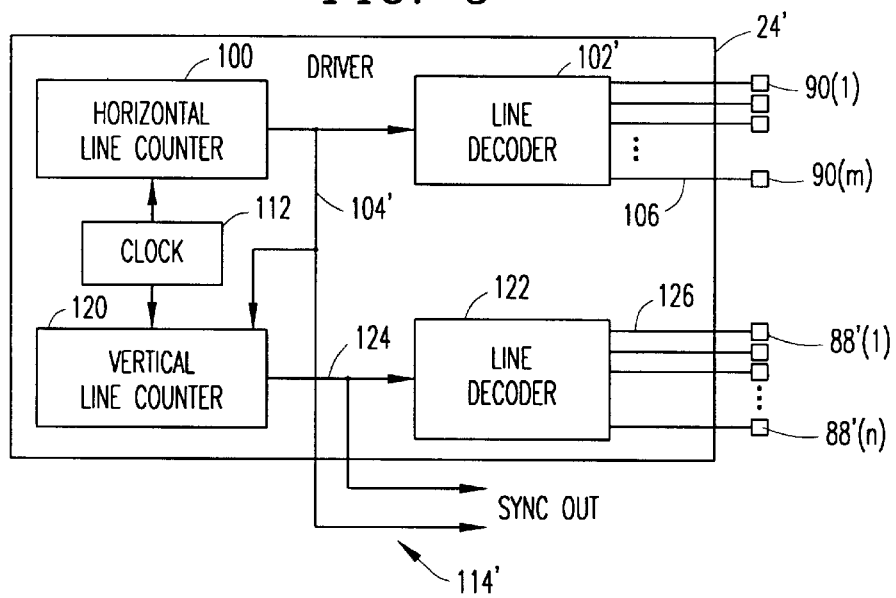
FIG. 7 is a simplified block diagram of another embodiment for a driver circuit for the imaging system of FIGS. 2 and 6.

Reference is now made to FIG. 7 wherein there is shown a block diagram of another embodiment of the driver circuit 24' useful with the modulator 70' of FIG. 6 (where identical reference numbers refer to identical components). The driver circuit 24' operates to control the application of voltages to the strip electrodes 88' and 90. More specifically, a horizontal line counter 100' resets at the instigation of each scan, and then cycles from 1 to m to count through the number of strip electrodes 90. A line decoder 102' receives a digital signal 104' from the line counter 100' that corresponds to the count in the horizontal line counter. The digital signal 104' is then decoded to generate an electrode voltage signal 106 on one output at a time. Responsive to each increment of the horizontal line counter 100' digital signal 104', a vertical line counter 120 resets and then cycles from 1 to m to count through the number of strip electrodes 88'. A line decoder 122 receives a digital signal 124 from the vertical line counter 120 that corresponds to the count in the vertical line counter. The digital signal 124 is then decoded to generate an electrode voltage signal 126 on one output at a time. Application of these electrode voltage signals 106 and 126, as discussed above, causes the second polarity (associated with a second alignment of the liquid crystal 80) to be applied between a selected pair of strip electrodes 88' and 90 which frustrates total internal reflection within the waveguide 50 and opens the corresponding optical door 72 located at the intersection of the selected strip electrodes. While this occurs, the light generator 56 supplies the scanning light 60, and the incident beam of light 20 generated at the pixel location 18 in the imaging system 12 array that corresponds to the open optical door 72 (i.e., at the intersection of the two activated strip electrodes 88' and 90. This further allows for reception of the emission beam of light 22/22' back into the waveguide. The rate at which the line counters 100' and 120 increment to select strip electrodes 88' and 90 may be user selected, with control over such rate provided through a clock 112. Responsive to operation of the counters 100' and 120, and decoders 102' and 122, the imaging system 12 effectively scans each well 16 on the assay plate 14. By repeating the foregoing process operation, multiple consecutive scans of the plate 14 may be performed. It will further be understood that the light source driver 108 may simultaneously energize each of the point sources 110 causing a plurality of incident beams of light 20 to be output from each pixel location 18 along the selected strip electrode 90. With this operation, a corresponding plurality of emission beams of light 22 will be simultaneously generated and propagated back through the waveguide 50, with the processor 26 (see, FIG. 1) operating to simultaneously capture or sequentially sample the corresponding data signals 76 output from the photoreceptors 74. The driver circuit 24 further outputs 114' one or more sync signals that provide information to the processor 26 concerning the strip electrodes 88'(1 to n) and 90(1 to m) that are currently being selected, and thus identify which optical door has been opened. This information is used by the processor to correlate received data signals 76 as output from the photoreceptors 74 of the imaging system 12 with the scanning operation being implemented by the driver circuit 24'.

Reference is now made to FIG. 8 wherein there is shown is a block diagram for another embodiment of an imaging system within the biochemical assay device shown in FIG. 1 (where identical reference numbers refer to identical components). Configuration and operation of the imaging system mimics that previously described in connection with FIG. 2. FIG. 8 more specifically illustrates that the incident beam of light 20 may utilize a different optical door to exit the waveguide than the optical door used by the emission beam of light 22' to re-enter the waveguide. FIG. 8 further more specifically illustrates that the light generator 56 and photoreceptor 74' need not necessarily be co-located. In this regard, the photoreceptor 74' may be positioned on an edge of the waveguide that is opposite the edge placement of the light generator 56. Alternatively, the photoreceptor 74' may be positioned on an edge of the waveguide that is adjacent the edge placement of the light generator 56. FIG. 8 still further illustrates that the emission beam of light 22' may propagate within the waveguide by total internal reflection in substantially the same direction as the propagation of the scanning beam 60. It is also recognized that this propagation, although not explicitly illustrated due to the two-dimensional nature of the drawing, should be understood to also encompass a propagation in a direction perpendicular to the direction of propagation for the scanning beam 60.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

We claim:

1. A biochemical assay device for optically scanning individual wells in an assay plate, comprising:
   an imaging system including:
      a light propagating substrate for overlaying the assay plate;
      a plurality of pixel locations defined on the substrate, each pixel location aligned with a well in the assay plate;
      means for selectively outputting from the light propagating substrate an incident beam of light at each pixel location to individually scan each of the wells in the assay plate, wherein an emission beam of light is generated from the scanned well in response to illumination by the incident beam of light; and
      means for detecting the emission beam of light from each scanned well;
   a driver circuit operable to control the selective outputting of the incident beams of light and to control the selective receiving of the emission beams of light; and
   a processing circuit to process the detected emission beams of light for purposes of assaying a biological sample contained in each scanned well.

2. The device as in claim 1 wherein the imaging system further includes a light generator coupled to the light propagating substrate that generates a scanning light having a certain wavelength that is used by the means for selectively outputting to generate the incident beams of light from each pixel location.

3. The device as in claim 2 wherein the scanning light propagates through the light propagating substrate by total internal reflection.

4. The device as in claim 3 wherein the means for selectively outputting comprises means for selectively effectuating a frustration of the total internal reflection of the scanning light at individual pixel locations to illuminate each of the wells in the assay plate with the incident beam of light.

5. The device as in claim 4 wherein the means for selectively effectuating frustration of the total internal reflection of the scanning light at each pixel location comprises a refractive index modulator.

6. The device as in claim 2 wherein the means for detection comprises a photoreceptor coupled to the light propagating substrate to measure each emission beam of light output from a scanned well.

7. The device as in claim 2 wherein the means for detection comprises a photoreceptor coupled to the assay plate adjacent the scanned well to measure each emission beam of light output from a scanned well.

8. The device as in claim 2 wherein the emission beam of light propagates through the light propagating substrate by total internal reflection to the means for detecting.

9. The device as in claim 8 wherein the means for selectively outputting comprises means for selectively effectuating a frustration of the total internal reflection at each pixel location to allow the emission beam of light generated from each of the scanned wells in the assay plate to enter the light propagating substrate.

10. The device as in claim 9 wherein the means for selectively effectuating frustration of the total internal reflection at each pixel location comprises a refractive index modulator.

11. The device as in claim 8 wherein the scanning light propagates through the light propagating substrate by total internal reflection and each of the emission beams of light propagates by total internal reflection in a reverse direction.

12. The device as in claim 11 wherein the same pixel location is used to generate the incident beam of light from the light propagating substrate and allow entry of the emission beam of light back into the light propagating substrate.

13. An imaging system, comprising:
   an optical waveguide having a scanning surface;
   a light generator coupled to the optical waveguide and directing a scanning light beam into the optical waveguide at an angle that causes the scanning light beam to propagate within the optical waveguide by total internal reflection;
   a refractive index modulator positioned adjacent the scanning surface, the modulator including a plurality of optical doors, each optical door being selectively configurable into either a first refractive condition or a second refractive condition, wherein the first refractive condition causes the optical door to have a first index of refraction that reflects the scanning beam at the scanning surface, and wherein the second refractive condition causes the optical door to have a second index of refraction that allows the scanning light beam to exit the optical waveguide through the optical door at the scanning surface to illuminate a scanned object with an incident beam of light;
   wherein the scanned object responds to illumination by generating an emission beam of light; and
   a photoreceptor for receiving the emission beam of light.

14. The imaging system as in claim 13 wherein the plurality of optical doors are arranged in an array format.

15. The imaging system as in claim 13 wherein the emission beam of light enters the optical waveguide through an optical door, and wherein the optical door through which the scanning light beam exits the optical waveguide and the optical door through which the emission beam of light enters the waveguide comprise the same optical door.

16. The imaging system as in claim 13 wherein the emission beam of light enters the optical waveguide through an optical door, and wherein optical door through which the scanning light beam exits the optical waveguide and the optical door through which the emission beam of light enters the waveguide comprise different optical doors.

17. The imaging system as in claim 13 wherein the emission beam of light propagates through the optical waveguide by total internal reflection.

18. The imaging system as in claim 17 wherein the scanning light beam and the emission beam of light each propagate by total internal reflection in an opposite direction.

19. The imaging system as in claim 13 wherein the second index of refraction frustrates the total internal reflection propagation of the scanning light beam at the optical door.

20. The imaging system as in claim 13 wherein the scanned object is a well of an assay plate and the photoreceptor is coupled to the optical waveguide to measure each emission beam of light output from a scanned well.

21. The imaging system as in claim 13 wherein the scanned object is a well of an assay plate and the photoreceptor is coupled to the assay plate adjacent the scanned well to measure each emission beam of light output from a scanned well.

22. A method for optically scanning individual wells in an assay plate, comprising the steps of:

overlaying a light propagating substrate on the assay plate, the substrate including a plurality of pixel locations, each pixel location being aligned with a well in the assay plate;

propagating a scanning light within the light propagating substrate by total internal reflection;

frustrating the total internal reflection of the scanning light at each pixel location to output from the light propagating substrate an incident beam of light at each pixel location that illuminates each of the wells in the assay plate, with each illuminated well generating an emission beam of light in response to the incident beam of light; and detecting the propagating emission beams of light.

23. The method of claim 22 further including the steps of:

receiving the emission beam of light by the light propagating substrate; and propagating the received emission beams of light through the light propagating substrate for detection.

24. The method of claim 23 further including the step of propagating the received emission beams of light by passing the emission beams of light through the light propagating substrate for detection.

25. The method of claim 23 further including the step of propagating the received emission beams of light through the light propagating substrate by total internal reflection.

26. The method of claim 25 wherein the step of propagating the emission beams of light by total internal reflection comprises the step of propagating in a reverse direction than the scanning light.

27. The method of claim 22 wherein the step of frustrating comprises the step of modulating a variable index of refraction material located at each pixel location adjacent the light propagating substrate.

28. The method of claim 22 wherein the step of detecting comprises the step of passing the emission beam of light through the light propagating substrate.

* * * * *